United States Patent [19]

Annarelli et al.

[11] Patent Number: 4,681,964

[45] Date of Patent: Jul. 21, 1987

[54] METHOD OF INCREASING THE REACTIVITY OF PHOSPHORUS PENTASULFIDE

[75] Inventors: Dennis C. Annarelli, Newtown, Pa.; Frank J. Dominiani, Jr., Flemington, N.J.

[73] Assignee: FMC Corporation, Philadelphia, Pa.

[21] Appl. No.: 700,208

[22] Filed: Feb. 11, 1985

[51] Int. Cl.$^4$ .............................................. C07F 9/165
[52] U.S. Cl. .................................................... 558/112
[58] Field of Search ......................... 260/981; 558/112

[56] References Cited

U.S. PATENT DOCUMENTS

| | | | |
|---|---|---|---|
| 2,534,217 | 12/1950 | Bartleson | 252/46.6 |
| 2,553,588 | 5/1951 | Hughes | 252/46.6 |
| 3,403,201 | 9/1968 | Adrian et al. | 260/981 |
| 3,828,084 | 8/1974 | Kaplan et al. | 260/399 |
| 3,848,032 | 11/1974 | Le Suer et al. | 260/981 |
| 4,083,899 | 4/1978 | Demarcq | 260/981 |

*Primary Examiner*—Anton H. Sutto
*Attorney, Agent, or Firm*—Frank Ianno; Eugene G. Seems

[57] ABSTRACT

The alcoholysis and phenolysis of phosphorus pentasulfide is accelerated by reacting the phosphorus pentasulfide with an alcohol or phenol in the presence of a catalytic amount of a catalyst consisting essentially of water, phosphoric acid, a phosphate salt, sulfuric acid or mixtures thereof. The dialkyl- or diaryldithiophosphoric acids produced are useful in the production of such products as motor oil additives, insecticides, etc.

10 Claims, No Drawings

METHOD OF INCREASING THE REACTIVITY OF PHOSPHORUS PENTASULFIDE

This invention relates to a method for accelerating the alcoholysis and phenolysis of phosphorus pentasulfide.

In the production of additives for motor oils and phosphorus-containing insecticides, phosphorus pentasulfide is used extensively in the preparation of the intermediates O,O-dialkyl- or O,O-diaryldithiophosphoric acids. The hydroxyalkyl or hydroxyaryl compound used in the preparation of the intermediate will vary dependent upon the properties desired in the ultimate product. In general, intermediates intended for the production of insecticides are prepared from the lower molecular weight hydroxy compounds such as methanol and ethanol. For motor oil additives, the hydroxy compounds selected generally contain from about 4 to about 8 carbon atoms and intermediates so prepared may be mixed with intermediates prepared from methanol and/or ethanol. In the formation of the motor oil additives, the dithiophosphoric acids are reacted with metal compounds, particularly compounds of the metals of Group IIB of the Periodic Table, to form compositions containing combined sulfide, organic and metal radicals.

The rate of reaction between an alcohol or a phenol and phosphorus pentasulfide varies depending upon the history of the phosphorus pentasulfide. Rapidly quenching molten pentasulfide by pouring it onto a cold metal plate or by pouring it into an inert high boiling point liquid may be used to increase the reactivity of the phosphorus pentasulfide. The quenching is believed to "freeze" the phosphorus pentasulfide into a high energy state by immobilizing the amorphous and crystalline constituents or phases due to the effects of rapidly increasing the viscosity as the pentasulfide passes from the molten state to the solid state. The quenched phosphorus pentasulfide contains much of the activation energy necessary for the alcoholysis and phenolysis reactions. From a practical standpoint, the quenching methods present difficult technical problems for the producer of the pentasulfide. Furthermore, the pentasulfide so treated exhibits a decrease in reactivity during storage, or in response to a rise in temperature, more rapidly than phosphorus pentasulfide of ordinary reactivity.

An alternative method for increasing the reactivity of phosphorus pentasulfide involves the use of catalysts. From the users view, this method is more practical because in certain instances the ordinary reactivity is satisfactory and he need only use a catalyst where a higher reactivity is desired or required. A variety of catalysts have been proposed.

The present invention provides a simple, inexpensive method for accelerating the alcoholysis and phenolysis of phosphorus pentasulfide.

The present method contemplates the alcoholysis and phenolysis of phosphorus pentasulfide in the presence of a catalytic amount of a catalyst consisting essentially of water, phosphoric acid and its salts, sulfuric acid and mixtures thereof. The enhancement of the reactivity increases rapidly up to the use of about 1% by weight of the phosphorus pentasulfide and the rate of increase decreases with increases above about 1%. The catalyst may be used in amounts up to about 5%.

The efficacy of the catalysts was measured by the standard phosphorus pentasulfide reactivity Monsanto (isopropanol) method. In this method, a 650 ml dewar flask is fitted with a rubber stopper having two apertures to accommodate a temperature measuring device and the shaft of a mechanical stirrer. The flask is mounted in a constant temperature bath maintained at $30.0 \pm 0.1°$ C. with stirring at 100 RPM. To establish the reactivity of a given sample of phosphorus pentasulfide, the flask was charged with $100 \pm 1$ ml anhydrous isopropanol. When the isopropanol held at $30 \pm 0.1°$ C., $36.00 \pm 0.01$ g of the phosphorus pentasulfide in a finely granulated form was added and the time followed until the maximum temperature was reached and then a decrease of a few tenths degree decline had occurred. The time at which the maximum temperature was obtained is noted as $t_f$.

The reactivity was then determined, expressed in °C./minute as:

$$R = \frac{T_f - T_o}{t_f - t_o}$$

where
$T_f$ = highest temperature
$T_o$ = initial temperature $30.0 \pm 0.1°$ C.
$t_f$ = time at which maximum temperature is obtained
$t_o$ = time at which $P_2S_5$ is added Following the determination of the reactivity of a sample of phosphorus pentasulfide, the enhancement of the reactivity imparted by a catalyst was determined in the same manner. In these determinations, the amount of the specific catalyst was added to $100 \pm 1$ ml anhydrous isopropanol and $36.00 \pm 0.01$ g of phosphorus pentasulfide added. The enhancing effect can be expressed as an absolute increase, $\Delta°$C./min, or in relative terms, % increase.

The improvement in reactivity imparted by catalysts contemplated by the present method was determined on three lots of phosphorus pentasulfide; A—reactivity 5.14, B—reactivity 1.75 and C—reactivity 1.19. The specific catalysts and amounts used are shown in Tables I, II and III. Of the catalysts, the most effective are the mixtures of phosphoric acid ($H_3PO_4$) and water, mixtures ranging from 25% to 105% $H_3PO_4$. Preferably, the amount of catalyst is about 1% based upon the weight of the phosphorus pentasulfide.

The effect of the $H_3PO_4$ to water ratio was determined at the 1% catalyst level on a freshly prepared lot of phosphorus pentasulfide, D, having a reactivity of $R = 0.88°$ C./min. The results of these determinations are shown in Table IV.

A lot of phosphorus pentasulfide, E, having a reactivity of $R = 2°$ C./min was exposed to atmospheric moisture for a period of 4 months at which time the reactivity had increased to $3.02°$ C./min. The effect of the $H_3PO_4$ to water ratio was determined at the 1% catalyst level on the 4 month phosphorus pentasulfide. The results of these determinations are shown in Table V.

Although the catalyst may be present in amounts up to about 5% based upon the weight of the phosphorus pentasulfide, the preferred amount is from about 0.5% to about 1%. Amounts exceeding about 1% do not effect substantial increases in the rate of reactivity in proportion to the increase in the amount of catalyst. The preferred catalysts are the mixtures of $H_3PO_4$ and water containing from about 50% to about 85% phosphoric acid although concentrations of 25% up to 105% $H_3PO_4$ are entirely satisfactory. The most preferred amount and concentration of the acid is 1% of 85% phosphoric acid.

It will be noted that in certain instances, such as in the use of sulfuric acid as the catalyst, when the catalyst is present in amounts under about 0.5% a slight reduction in reactivity of the phosphorus pentasulfide results. Such adverse affect is reversed readily by increasing the amount of catalyst and using at least 1%.

Although in Table III, only zinc phosphate is shown as a catalyst, other metal phosphates are satisfactory. In the production of additives for motor oils, the intermediates are generally reacted with a zinc compound, hence, the presence of zinc in the intermediates needs not be removed.

As stated hereinbefore, the preferred catalysts are mixtures of $H_3PO_4$ and water. As shown by the data in Tables IV and V, the combinations of water and $H_3PO_4$ result in reactivity enhancement greater than could be predicted by the simple addition of their expected contributions. It will be noted the reactivity shown in Example 28, 25% $H_3PO_4$ is substantially identical to the reactivity shown in Example 33, 105% $H_3PO_4$. Examples 35 and 40 show the same effect on reactivity. As the proportion of water decreases and the proportion of $H_3PO_4$ increases, the reactivity increases. As shown by Examples 32 and 33 and Examples 39 and 40, as the proportion of $H_3PO_4$ increases above 85% and when it reaches 105%, the reactivity decreases to about that obtained when the $H_3PO_4$-water mixture contains 25% $H_3PO_4$.

The catalysts are highly effective, inexpensive, readily available and present no difficulties in handling. They are conveniently added to the alcohol or phenol prior to reaction with the phosphorus pentasulfide.

TABLE I

Isopropanol - $P_2S_5$ Lot A

| Example | Catalyst | Weight Percent Catalyst (based on $P_2S_5$) | R (°C./min) | ΔR (°C./min) | ΔR (%) |
|---|---|---|---|---|---|
| 1 | None | 0 | 5.14 | 0 | 0 |
| 2 | 85% $H_3PO_4$ | 0.1 | 6.99 | 1.85 | 36 |
| 3 | 85% $H_3PO_4$ | 0.25 | 9.22 | 4.08 | 79 |
| 4 | 85% $H_3PO_4$ | 0.50 | 10.66 | 5.52 | 107 |
| 5 | 85% $H_3PO_4$ | 1 | 10.36 | 5.22 | 102 |
| 6 | 85% $H_3PO_4$ | 5 | 10.79 | 5.65 | 110 |
| 7 | $H_2O$ | 1 | 5.99 | 0.85 | 17 |
| 8 | $H_2O$ | 5 | 8.24 | 3.10 | 60 |
| 9 | 98% $H_2SO_4$ | 0.1 | 4.93 | −0.21 | −0.04 |
| 10 | 98% $H_2SO_4$ | 0.25 | 4.83 | −0.31 | −0.06 |
| 11 | 98% $H_2SO_4$ | 1 | 9.13 | 3.99 | 78 |

TABLE II

Isopropanol - $P_2S_5$ Lot B

| Example | Catalyst | Weight Percent Catalyst (based on $P_2S_5$) | R (°C./min) | ΔR (°C./min) | ΔR (%) |
|---|---|---|---|---|---|
| 12 | None | 0 | 1.75 | 0 | 0 |
| 13 | 85% $H_3PO_4$ | 0.1 | 2.19 | 0.44 | 25 |
| 14 | 85% $H_3PO_4$ | 0.25 | 2.61 | 0.86 | 49 |
| 15 | 85% $H_3PO_4$ | 0.50 | 3.09 | 1.34 | 77 |
| 16 | 85% $H_3PO_4$ | 1 | 3.69 | 1.94 | 111 |
| 17 | 85% $H_3PO_4$ | 5 | 4.04 | 2.31 | 132 |
| 18 | $H_2O$ | 1 | 2.33 | 0.58 | 33 |
| 19 | $H_2O$ | 5 | 2.87 | 1.12 | 64 |
| 20 | 98% $H_2SO_4$ | 0.1 | 1.73 | −0.02 | −0.01 |

TABLE III

Isopropanol - $P_2S_5$ Lot C

| Example | Catalyst | Weight Percent Catalyst (based on $P_2S_5$) | R (°C./min) | ΔR (°C./min) | ΔR (%) |
|---|---|---|---|---|---|
| 21 | None | 0 | 1.19 | 0 | 0 |
| 22 | 85% $H_3PO_4$ | 1 | 2.07 | 0.88 | 74 |
| 23 | 105% $H_3PO_4$ | 1 | 1.76 | 0.57 | 48 |
| 24 | $Zn_3(PO_4)_2$ | 1 | 1.30 | 0.11 | 9 |
| 25 | $Zn_3(PO_4)_2$ | 1.67 | 1.48 | 0.29 | 24 |
| 26 | 98% $H_2SO_4$ | 1 | 1.25 | 0.06 | 0.05 |

TABLE IV

Isopropanol - $P_2S_5$ Lot D

| Example | Catalyst | Weight Percent Catalyst (based on $P_2S_5$) | R (°C./min) | ΔR (°C./min) | ΔR (%) |
|---|---|---|---|---|---|
| 27 | — | 0 | 0.88 | — | — |
| 28 | 25% $H_3PO_4$ | 1.0 | 1.31 | 0.43 | 49 |
| 29 | 50% $H_3PO_4$ | 1.0 | 1.41 | 0.53 | 60 |
| 30 | 58% $H_3PO_4$ | 1.0 | 1.41 | 0.53 | 60 |
| 31 | 70% $H_3PO_4$ | 1.0 | 1.46 | 0.58 | 66 |
| 32 | 85% $H_3PO_4$ | 1.0 | 1.58 | 0.70 | 80 |
| 33 | 105% $H_3PO_4$ | 1.0 | 1.32 | 0.44 | 50 |

TABLE V

Isopropanol - $P_2S_5$ Lot E

| Example | Catalyst | Weight Percent Catalyst (based on $P_2S_5$) | R (°C./min) | ΔR (°C./min) | ΔR (%) |
|---|---|---|---|---|---|
| 34 | — | 0 | 3.02 | — | — |
| 35 | 25% $H_3PO_4$ | 1.0 | 3.63 | 0.61 | 20 |
| 36 | 50% $H_3PO_4$ | 1.0 | 3.70 | 0.68 | 23 |
| 37 | 58% $H_3PO_4$ | 1.0 | 4.27 | 1.25 | 41 |

TABLE V-continued

| | | Isopropanol - $P_2S_5$ Lot E | | | |
|---|---|---|---|---|---|
| Example | Catalyst | Weight Percent Catalyst (based on $P_2S_5$) | R (°C./min) | ΔR (°C./min) | ΔR (%) |
| 38 | 70% $H_3PO_4$ | 1.0 | 4.24 | 1.22 | 40 |
| 39 | 85% $H_3PO_4$ | 1.0 | 4.25 | 1.23 | 41 |
| 40 | 105% $H_3PO_4$ | 1.0 | 3.70 | 0.68 | 23 |

What is claimed is:

1. The method for accelerating the alcoholysis or phenolysis of phosphorus pentasulfide which comprises contacting phosphorus pentasulfide with an alcohol or phenol in the presence of a catalytic amount of a catalyst consisting essentially of a member selected from the group consisting of water, phosphoric acid and its metal salts, and sulfuric acid.

2. The method of claim 1 wherein the amount of catalyst is up to about 5% by weight based upon the weight of the phosphorus pentasulfide.

3. The method of claim 2 wherein the catalyst consists of 85% $H_3PO_4$ and the amount of the catalyst is 1% by weight based upon the phosphorus pentasulfide.

4. The method of claim 1 wherein the amount of catalyst is from about 0.5% to about 1% by weight based upon the weight of the phosphorus pentasulfide.

5. The method of claim 4 wherein the catalyst is 98% sulfuric acid.

6. The method for accelerating the alcoholysis or phenolysis of phosphorus pentasulfide which comprises contacting phosphorus pentasulfide with an alcohol or phenol in the presence of a catalytic amount, up to 5% by weight based upon the weight of the phosphorus pentasulfide, of phosphoric acid of a concentration of 25% to 105% $H_3PO_4$.

7. The method of claim 6 wherein the amount of phosphoric acid is from about 0.5% to 1% by weight based upon the phosphorus pentasulfide and the concentration of the phosphoric acid is from about 50% to about 85% $H_3PO_4$.

8. The method for accelerating the alcoholysis or phenolysis of phosphorus pentasulfide which comprises contacting phosphorus pentasulfide with an alcohol or phenol in the presence of a catalytic amount, up to 5% by weight based on the weight of the phosphorus pentasulfide, of zinc phosphate.

9. The method for accelerating the alcoholysis or phenolysis of phosphorus pentasulfide which comprises contacting phosphorus pentasulfide with an alcohol or phenol in the presence of a catalytic amount, up to 5% by weight based upon the weight of the phosphorus pentasulfide, of water.

10. The method for accelerating the alcoholysis or phenolysis of phosphorus pentasulfide which comprises contacting phosphorus pentasulfide with an alcohol or phenol in the presence of a catalytic amount, from at least 1% up to 5% by weight based upon the weight of the phosphorus pentasulfide, of sulfuric acid.

* * * * *